(12) United States Patent
Couffin et al.

(10) Patent No.: US 8,785,417 B2
(45) Date of Patent: Jul. 22, 2014

(54) ABSORBENT HYDROPHOBIC BORONATE GALACTOMANNAN COMPLEXES AND PROCESS FOR PRODUCING SAME

(75) Inventors: Anne-Claude Couffin, Montréal (CA);
Mohammed Berrada, Longueuil (CA);
André Laforest, Longueuil (CA);
Nicolas Nourry, St-Amable (CA)

(73) Assignee: Archer Daniels Midland Co., Decatur, IL (US)

( * ) Notice: Subject to any disclaimer, the term of this patent is extended or adjusted under 35 U.S.C. 154(b) by 0 days.

(21) Appl. No.: 12/367,029

(22) Filed: Feb. 6, 2009
(Under 37 CFR 1.47)

(65) Prior Publication Data
US 2010/0042063 A1    Feb. 18, 2010

Related U.S. Application Data

(63) Continuation of application No. 10/596,578, filed as application No. PCT/CA2006/000772 on May 12, 2006.

(51) Int. Cl.
| | |
|---|---|
| *B01J 20/26* | (2006.01) |
| *A61L 15/60* | (2006.01) |
| *A61L 15/18* | (2006.01) |
| *A61L 15/28* | (2006.01) |
| *B01J 20/24* | (2006.01) |

(52) U.S. Cl.
CPC ............... *A61L 15/60* (2013.01); *B01J 20/26* (2013.01); *A61L 15/18* (2013.01); *A61L 15/28* (2013.01); *B01J 20/262* (2013.01); *B01J 2220/4825* (2013.01); *B01J 20/24* (2013.01)
USPC .......... 514/54; 536/114; 536/123; 536/123.1; 507/110

(58) Field of Classification Search
CPC ................................................ A23V 2250/505
USPC ........... 536/114, 123, 123.1; 507/110; 514/54
See application file for complete search history.

(56) References Cited

U.S. PATENT DOCUMENTS

| | | | | |
|---|---|---|---|---|
| 3,722,595 | A * | 3/1973 | Kiel | 166/308.4 |
| 4,333,461 | A * | 6/1982 | Muller | 604/368 |
| 6,133,193 | A * | 10/2000 | Kajikawa et al. | 502/402 |
| 7,985,742 | B2 * | 7/2011 | Bergeron | 514/60 |

OTHER PUBLICATIONS

Bishop et al ("Determination of the mode and efficacy of the cross-linking of guar by borate using MAS B NMR of borate cross-linked guar in combination with solution B NMR of model systems," Dalton Transactions, 17:2621-2634, 2004).*

Coveney et al ("Novel approaches to cross-linking high molecular weight polysaccharides: Application to guar-based hydraulic fracturing fluids," Molecular Simulation, 25:265-299, 2000).*

* cited by examiner

*Primary Examiner* — Brandon Fetterolf
*Assistant Examiner* — Everett White

(57) ABSTRACT

Absorbent boronate-galactomannan complexes comprising a hydrophobic group are disclosed. The boronate-galactomannan complexes are solid materials capable of gel forming upon contacting with liquids. The boronate-galactomannan complexes are particularly suitable for absorbing liquids.

16 Claims, 1 Drawing Sheet

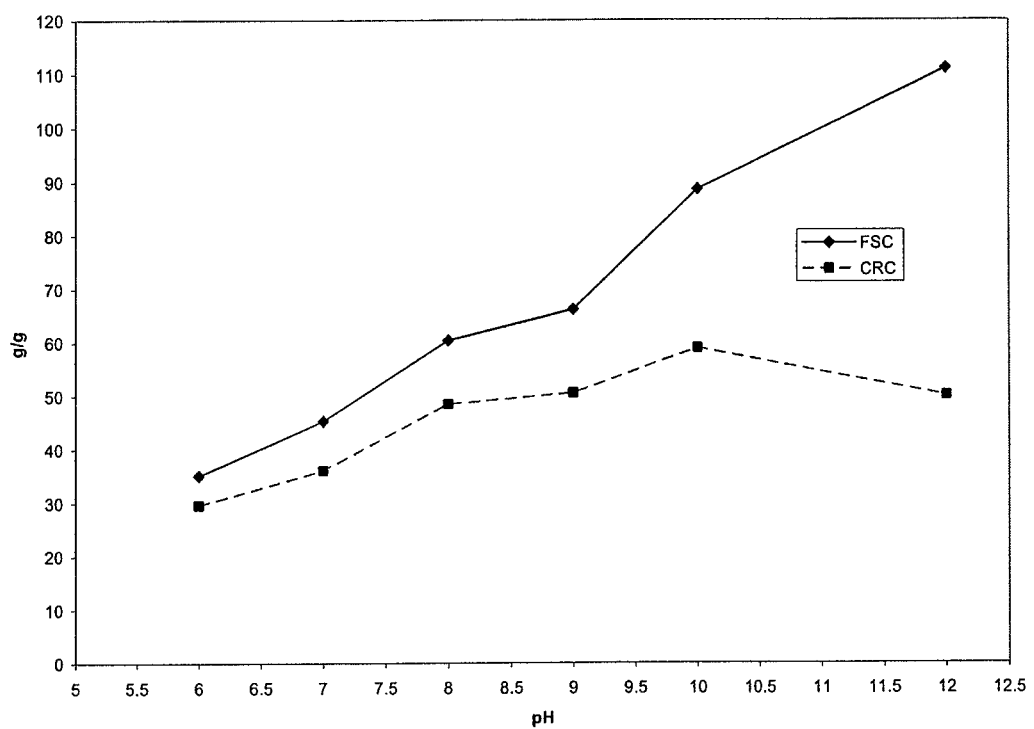

ABSORBENT HYDROPHOBIC BORONATE GALACTOMANNAN COMPLEXES AND PROCESS FOR PRODUCING SAME

The present application is a continuation of co-pending U.S. application Ser. No. 10/596,578 filed Jun. 16, 2006, which is a national phase application under 35 U.S.C. §371 of International Application No. PCT/CA2006/000772, filed May 12, 2006, which claims the benefit of Canadian Application No. 2,507,121, filed May 12, 2005, the entire contents of these applications are incorporated by reference.

FIELD OF THE INVENTION

The present teachings relate to absorbent hydrophobic galactomannan complexes. More specifically, but not exclusively, the present teachings relates to absorbent hydrophobic boronate galactomannan complexes and to a process for producing same.

BACKGROUND OF THE INVENTION

Water absorbent materials, such as superabsorbent polymers, can be employed in various applications such as in disposable sanitary products (i.e. diapers, incontinence articles, feminine hygiene products, airlaids and absorbent dressings), household articles, sealing materials, humectants in agricultural products for soil conditioning, in oil-drilling fluids (i.e. lost-circulation material, fracturing fluids), anti-condensation coatings, in agricultural, horticultural and forestry applications for retaining water in the soil and for the release of water to the roots of plants and trees, in the textile industry, in printing applications, in absorbent paper products, in bandages and surgical pads (i.e. wound dressings), in ore treatments, in pet litter, in water treatment, in food pads (i.e. applications related to the transportation of fresh food and food packaging), in detergents, in fire-fighting gels, in sealing materials, as chemical absorbents for the cleanup of acidic and/or basic aqueous spills including water soluble chemical spills, as polymeric gels for the slow and controlled release of cosmetics and pharmaceuticals (also known as drug delivery systems), as airlaids, and finally in the manufacture of artificial snow. However, the primary use of superabsorbent polymers, also referred to a "SAPs", is in disposable personal hygiene products. Such products include, in increasing order of volume of superabsorbent materials used, diapers, training pants, adult incontinence products and feminine hygiene products.

Increased oil prices have had a negative impact on the superabsorbent industry such that natural polysaccharide-based superabsorbents have become an attractive alternative. Such natural superabsorbent materials can be readily obtained from renewable sources such as starch. Various absorbent compositions comprising polysaccharide-based superabsorbents have been proposed by Le Group Lysac Inc. Huppé et al. (CA 2,308,537) teach the use of biodegradable, glass-like pregelatinized starch as absorbents for liquids. Couture et al. (CA 2,362,006) teach the use of oligomeric polyethylene glycol crosslinked polysaccharides, in particular polyethylene glycol crosslinked starch as absorbent materials. Thibodeau et al. (CA 2,462,053) teach the use of crosslinked amylopectin as absorbent materials. Bergeron et al. (CA 2,426,478) teach the use of modified starches (i.e. crosslinked amylopectin) and mannose containing polysaccharides, ionic polysaccharides, gelling proteins and mixtures thereof in formulating absorbent materials. Berrada et al. (CA 2,483,049) teach the use of phylosilicates dispersed in an absorbent polysaccharide matrix, as having absorbent characteristics. Berrada (CA 2,519,417) teaches the use of guanidinated polysaccharides as absorbent materials.

The use of galactomannans, essentially cross-linked with borate, titanium or zirconium ions, as superabsorbent polysaccharides, has been disclosed in a number of patents: U.S. Pat. No. 3,661,154; U.S. Pat. No. 3,903,889; U.S. Pat. No. 4,624,868; U.S. Pat. No. 4,333,461; U.S. Pat. No. 5,532,350; U.S. Pat. No. 5,801,116; JP 2004-089401; JP 2004-075773; JP 2004-073370; JP 2004-066203; JP 2003-311150; JP 2003-154262; JP 2002-253961; JP 2002-035037; JP 2001-278998; JP 2002-037924; JP 2002-053859; JP 2001-120992; JP 2002-053859; JP 2001-226525 and JP 2001-122905. However, these polysaccharides suffer from syneresis and gel flowing problems. Crosslinking will seriously limit the manipulation of the absorbent materials, especially when shear thinning behavior is desired.

Complexes of aliphatic boronates with galactomannans have been disclosed by Bavouzet et al. (WO 97/47658). Complexes of aromatic boronates with galactomannans were disclosed by Bishop et al. (*Dalton Transactions;* 17; 2004; 2621-2634). PEG-diboronate galactomannan complexes have been disclosed by Coveney et al. (Molecular simulation, 2000, Vol. 25, pp. 265-299). Synthetic boronate polymer complexes with polysaccharides have also been disclosed by Miyazaki et al. (EP 0424168); Filipini (EP 0159521); Pelton et al. (WO 06/010268); and Destarac et al. (FR 2839723). However, these complexes were not disclosed as being absorbent materials.

There thus remains a need for absorbent hydrophobic boronate galactomannan complexes, as well as a process for producing same.

The present teachings seek to meet these and other needs.

The present teachings refer to a number of documents, the content of which is herein incorporated by reference in their entirety.

SUMMARY OF THE INVENTION

The present teachings broadly relate to novel absorbent or superabsorbent materials. More specifically, as broadly claimed, the present teachings relate to boronate-galactomannan complexes comprising a hydrophobic group, the boronate-galactomannan complexes having absorbent properties suitable for use in personal hygiene products. In an embodiment, the boronate-galactomannan complexes of the present teachings are dry, solid materials having good fluid-swelling properties and capable of gel forming upon contacting with a liquid.

In a further embodiment, the present teachings relate to the use of the boronate-galactomannan complexes comprising a hydrophobic group as absorbents in disposable sanitary products (i.e. diapers, incontinence articles, feminine hygiene products, airlaids and absorbent dressings), household articles, sealing materials, humectants in agricultural products for soil conditioning, in oil-drilling fluids (i.e. lost-circulation material, fracturing fluids), anti-condensation coatings, in agricultural, horticultural and forestry applications for retaining water in the soil and for the release of water to the roots of plants and trees, in the textile industry, in printing applications, in absorbent paper products, in bandages and surgical pads (i.e. wound dressings), in ore treatments, in pet litter, in water treatment, in food pads (i.e. applications related to the transportation of fresh food and food packaging), in detergents, in fire-fighting gels, in sealing materials, as chemical absorbents for the cleanup of acidic and/or basic aqueous spills including water soluble chemical spills, as polymeric gels for the slow and controlled release of cosmetics and pharmaceuticals (also known as drug delivery systems), as airlaids, and finally in the manufacture of artificial snow.

In a further embodiment, the present teachings relate to the use of the boronate-galactomannan complexes comprising a hydrophobic group as absorbents for liquids, non-limitative examples of which include water, aqueous solutions, physiological fluids and saline solutions.

In yet a further embodiment, the present teachings relate to compositions including at least one boronate-galactomannan complex comprising a hydrophobic group, and a co-absorbent material.

Finally, in a further embodiment, the present teachings relate to processes for preparing boronate-galactomannan complexes, the boronate-galactomannan complexes comprising a hydrophobic group.

The foregoing and other objects, advantages and features of the present teachings will become more apparent upon reading of the following non restrictive description of illustrative embodiments thereof, given by way of example only with reference to the accompanying drawings.

BRIEF DESCRIPTION OF THE DRAWINGS

In the appended drawings:

FIG. 1 is a graph illustrating the pH effect on the performance characteristics of a boronate-galactomannan complex comprising a hydrophobic group, according to an embodiment of the present teachings.

DETAILED DESCRIPTION OF ILLUSTRATIVE EMBODIMENTS

In order to provide a clear and consistent understanding of the terms used in the present specification, a number of definitions are provided below. Moreover, unless defined otherwise, all technical and scientific terms as used herein have the same meaning as commonly understood to one of ordinary skill in the art to which the present teachings pertain.

The use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

As used in this specification and claim(s), the term "about" is used to indicate that a value includes an inherent variation of error for the device or the method being employed to determine the value.

As used in this specification, the term "percent" or "%" refers to a percentage by weight (i.e. % (W/W)).

As used in this specification, the term "discrete particle" refers to individual particles.

As used in this specification, the term "Free Swell Capacity" (FSC), also called "Total Absorption", refers to the amount (g) of fluid absorbed per gram of the composition. Typical fluids are saline solutions (0.9% Weight/Weight NaCl solution, hereinafter called 0.9% NaCl solution or saline).

As used in this specification, the term "Centrifuge Retention Capacity" (CRC) also called "Retention", refers to the amount (g) of fluid retained per gram of the composition, following exposure of the composition to a centrifugation force of 250 G. Typical fluids are saline solutions (0.9% Weight/Weight NaCl solution, hereinafter called 0.9% NaCl solution or saline).

As used in this specification, the term "Absorption Under Load" (AUL), at 0.3 PSI, 0.7 PSI or 0.9 PSI, also called "Absorption Against Pressure" (AAP), refers to the amount (g) of fluid absorbed per gram of the composition under a given applied pressure. Typical fluids are saline solutions (0.9% Weight/Weight NaCl solution, hereinafter called 0.9% NaCl solution or saline).

The present description refers to a number of chemical terms and abbreviations used by those skilled in the art. Nevertheless, definitions of selected terms are provided for clarity and consistency.

As used in this specification, the term "absorbent material" or "absorbent polymer" refers to materials in a dry, solid state, having good fluid-swelling properties and capable of gel forming upon contacting with a fluid. Non limiting examples of such fluids are water, aqueous solutions, saline, or physiological fluids.

As used in this specification, the term "superabsorbent", "superabsorbent polymer" or "SAP" refers to absorbent materials capable of gel forming upon contacting with a fluid such as water, aqueous solutions, saline, or physiological fluids. Such materials are characterized a Centrifuge Retention Capacity (CRC) of at least 15 g/g.

As used in this specification, the term galactomannan" refers to naturally occurring polysaccharides comprising a poly β-(1-4)-mannose backbone having varying degrees of branching (DB), and to which single D-galactopyranosyl residues are attached via α-(1-6) linkages. Non-limiting examples of galactomannans are guar gum, locust bean gum, tara gum, fenugreek gum, mesquite gum and mixtures thereof. Endosperms of coffee (US 2004/0199943 A1), alfalfa, red-clover, and some soybeans (US 2004/0143871 A1) are also known to comprise galactomannans.

As used in this specification, the term "diol" refers to a pair of adjacent hydroxyl functions of galactomannans capable of reacting with complexing agents such as a boronate. Adjacent hydroxyl functions comprise a pair hydroxyl functions located on vicinal carbon atoms. As reported by Bishop et al. (*Dalton Transactions*; (17); 2004; 2621-2634), the 3,4 cis-diols on galactopyranosyl residues and the 2,3-cis-diols on the mannose backbone are diols capable of reacting with complexing agents (Scheme 1).

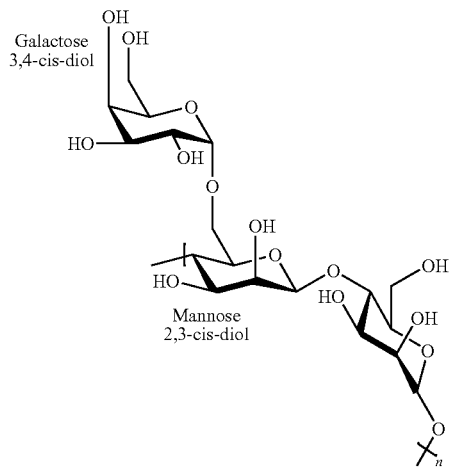

Scheme 1

As used in this specification, the term "boronate" or "boronates" refers to boron derivatives having the following general molecular structure:

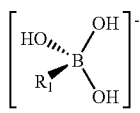

wherein $R_1$ is a hydrophobic group selected from the group consisting of aromatic groups, aliphatic groups and cyclic aliphatic groups.

As used in this specification, the term "complex" refers to boron-containing materials obtained by adding a boronate to a solution containing one or more galactomannans. The complexes of the present teachings are derived from interactions between the 3,4 cis-diols on galactopyranosyl residues and the 2,3-cis-diols on the mannose backbone with boronates. Complexes between such 3,4 cis-diols or 2,3-cis-diols and boronates are known as diol boronic ester linkages.

As used in this specification, the term "hydrophobic", "hydrophobic moiety" or "hydrophobic group" refers to those compounds, groups or moieties being immiscible in water.

As used in this specification, the term "hydrophilic", "hydrophilic moiety" or "hydrophilic group" refers to those compounds, groups or moieties being miscible in water.

As used in this specification, the term "amphiphilic", "amphiphilic moiety" or "amphiphilic group" refers to those compounds, groups or moieties having both hydrophilic and hydrophobic properties.

As used in this specification, the term "aliphatic" or "aliphatic group" refers to, and is inclusive of, all non-aromatic acyclic or cyclic groups. The aliphatic moieties may be saturated or unsaturated, and may be substituted. Non-limiting examples of aliphatic groups include alkyl groups, alkenyl groups, alkynyl groups, cycloalkyl groups, and cycloalkenyl groups.

As used in this specification, the term "alkyl" refers to straight, branched or substituted chain radicals having up to twenty carbon atoms. Non-limiting examples include methyl, ethyl, propyl, butyl, pentyl, hexyl, heptyl, octyl, nonyl, decyl, isopropyl, isobutyl, isopentyl, neopentyl, isohexyl, isodecyl, 3-methylpentyl, 2,3,4-trimethylhexyl, sec-butyl, tert-butyl, or tert-pentyl.

As used in this specification, the term "alkenyl" refers to straight, branched or substituted chain radicals of 2 to 10 carbon atoms having one or more double bonds.

As used in this specification, the term "alkynyl" refers to straight, branched or substituted chain radicals of 2 to 10 carbon atoms having one or more triple bonds.

As used in this specification, the term "cycloalkyl" refers to cyclic chain radicals, optionally branched or substituted, having up to ten carbon atoms. Non-limiting examples include cyclopropyl, cyclobutyl, cyclopentyl and cyclohexyl.

As used in this specification, the term "cycloalkenyl" refers to cyclic chain radicals, optionally branched or substituted, of 2 to 10 carbon atoms having one or more double bonds. Non-limiting examples include cyclopentenyl and cyclohexenyl.

As used in this specification, the term "aromatic", "aromatic groups" or "aromatic moiety" refers to unsaturated, conjugated, cyclic hydrocarbons containing one or more rings. Aromatic groups include 5- and 6-membered single-ring groups.

As used in this specification, the term "granular material", "granules", "particles", "powders", "grains" or "dusts" refers to particulate matter in a finely divided state. Granular material can include highly pulverized material with very small diameters. The particles need not be of any particular shape, but can be spherical, roughly spherical, cubic, or non regular in shape.

As used in this specification, the term "particle size" refers to the largest dimension of the particle. The particle size can be directly determined using sieving methods, optical or scanning electron microscopes as well as by other well-known methods. The particle size is often considered the diameter of the particle.

As used in this specification, the term "alkaline" refers to any pH greater than 7.0.

The present teachings broadly relate to absorbent boronate galactomannan complexes comprising a hydrophobic group. More specifically, the galactomannan is complexed with a boronate comprising a hydrophobic moiety. It was surprisingly discovered that such complexes exhibit absorbent characteristics similar to borax cross-linked galactomannans.

Efficient galactomannan-based absorbent materials are obtained by complexing the galactomannans with a boronate comprising a hydrophobic moiety. The hydrophobic moiety is selected from the group consisting of aromatic groups, aliphatic groups or cyclic aliphatic groups. Efficient absorbent materials are thus obtained without the need for cross-linking the galactomannans.

Boronates are well documented in the art to form complexes with the D-galactopyranosyl residues of galactomannans. Such D-galactopyranosyl residues are also known to be at the origin of the swelling characteristics of galactomannans. Hydrophobic pockets are created when a boronate comprising a hydrophobic moiety is complexed with the D-galactopyranosyl residues of galactomannans. Without being bound by any theory, it is believed that the hydrophobic pockets will become associated by means of weak Van der Waals interactions. Even though weak, it is believed that such interactions are sufficient to create a network of galactomannans having good swelling properties and efficient absorbent characteristics.

Gels of boronate-galactomannan complexes can be readily obtained by dispersing a galactomannan in an aqueous solution followed by the addition of a boronate comprising a hydrophobic moiety. The resulting reaction mixture is stirred at alkaline pH until gel formation. In an embodiment of the present teachings, an alkaline pH of at least 8.5 was used.

The boronates of the present teachings are amphiphilic in nature; the boronate, while bearing a hydrophobic moiety, being hydrophilic. Because of this amphiphilic character, the boronates only dissolve with great difficulty in water. However, the boronates readily dissolve in non-aqueous polar solvents, a non-limiting example of which includes tetrahydrofuran (THF).

The boronate-galactomannan complexes of the present teachings can be prepared in accordance with a process in which a galactomannan is dispersed in an aqueous solution, followed by the addition of a boronate comprising a hydrophobic moiety. The resulting boronate-galactomannan complex is then recovered by precipitation from one or more hydrophilic organic solvents. The precipitated boronate-galactomannan complex may then be optionally ground into a granular material having a particle size ranging from about 80 to about 800 µm.

In an embodiment of the present teachings, the boronate galactomannan complexes are in a dry solid state. Such dry boronate galactomannan complexes can be easily handled and stocked. In a further embodiment of the present teachings, the boronate galactomannan complexes are in a dry, solid granular state. In a further embodiment of the present teachings, the granular galactomannan complexes comprise a particle size ranging from about 80 to about 800 μm. In yet a further embodiment of the present teachings, the granular galactomannan complexes comprise a particle size ranging from about 150 to about 600 μm.

Dry boronate galactomannan complexes can be obtained by precipitating the complexes using hydrophilic organic solvents. Non-limiting examples of hydrophilic organic liquids as contemplated by the present teachings include $C_1$-$C_3$ alcohols, acetone, and acetonitrile. In an embodiment of the present teachings, the boronate galactomannan complexes are precipitated using methanol. Once precipitated, the boronate galactomannan complexes may further processed such as by grinding.

Non-limiting examples of galactomannans as contemplated by the present teachings include guar gum, locust bean gum, tara gum, fenugreek gum, mesquite gum and mixture thereof. The galactose to mannose ratio of galactomannans typically ranges from about 1:5 to about 1:1.

Guar gum, a typical galactomannan, is derived from ground endosperm of the guar plant, which is grown extensively in the semi-arid regions of Pakistan and India. As shown hereinabove in Scheme 1, the structure of guar gum comprises a random galactose to mannose ratio of about 1:1.6. This ratio is subject to fluctuations from crop to crop or from subspecies to subspecies (Jasinski et al. *J. Polym. Sci., part. B: Polym. Phys.* 1996, 34, 1477-1488).

Non-limiting examples of boronates as contemplated by the present teachings include phenyl boronate, phenethyl boronate, 2-naphtalen boronate, 3-biphenyl boronate, trans-1-octen-1-yl boronate and cyclohexyl boronate.

By virtue of their deficient valence, boronic acids possess a vacant p-orbital. This characteristic confers them unique properties as mild organic Lewis acids that can coordinate basic molecules. As such, boronates can be readily obtained from the corresponding boronic acids under alkaline conditions as illustrated in Scheme 2. Typical alkaline conditions comprise a pH of at least 8.5.

Scheme 2

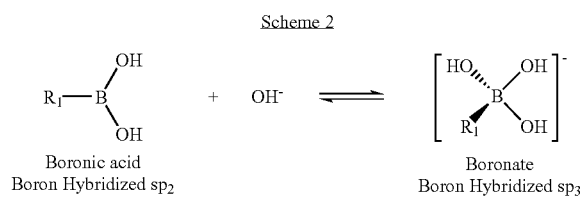

Boronic acid
Boron Hybridized sp$_2$

Boronate
Boron Hybridized sp$_3$

Boronic acid, bearing a hydrophobic group, is dissolved in a suitable solvent such as water, aqueous alkaline solutions or non-aqueous polar solvents such as tetrahydrofuran (THF). The solution may be heated to increase the boronic acid solubility. As reported in the literature (Bishop et al.; *Dalton Transactions*; (17); 2004; 2621-2634; Pezron, E. et al. *Macromolecules*, 1988, 21, 1121-1125; Jasinski et al., *J. Polym. Sci. Part B: Polym. Phys.*, 1996, 34, 1477-1488), the type of boronate species present in solution is directly dependent on the pH of the solution. It was observed that an alkaline pH was particularly suitable for generating boronates capable of complexing with galactomannans. Typical alkaline conditions comprise a pH of at least 8.5.

The absorbent boronate galactomannan complexes of the present teachings may be incorporated into absorbent personal hygiene products such as, for example, baby diapers, incontinence products, sanitary napkins and the like. They may be also used in absorbent members such as absorbent cores, airlaids or foamed structures.

The absorbent boronate galactomannan complexes of the present teachings may also be used in other applications such as in food pads, in agricultural and forestry applications for the retention of water in the soil and for the release of water to the roots of plants and trees; in fire-fighting techniques; in bandages and surgical pads; for the cleanup of acidic or basic solution spills, including water soluble chemical spills; as polymeric gels for the controlled release of cosmetics and pharmaceuticals (also known as drug delivery systems); and in artificial snow.

The absorbent boronate galactomannan complexes of the present teachings may be mixed with other co-absorbent materials to provide absorbent compositions. In an embodiment, the absorbent compositions comprise from about 1 to about 99% (w/w) of boronate galactomannan complex, and from about 99 to about 1% (w/w) of co-absorbent material. Non-limiting examples of co-absorbent materials include synthetic absorbent polymers, starch-based absorbents, ionic polysaccharides, fibers and mixtures thereof. In an embodiment of the present teachings, absorbent compositions are obtained by mixing one or more boronate galactomannan complexes with ionic polysaccharides; either cationic or anionic polysaccharides or mixtures thereof. In a further embodiment of the present teachings, absorbent compositions are obtained by mixing one or more boronate galactomannan complexes with one or more anionic polysaccharides.

Non-limiting examples of anionic polysaccharides as contemplated by the present teachings include carboxyalkyl polysaccharides, carboxymethyl cellulose, carboxymethyl starch, oxidized polysaccharides, xanthan, carrageenans, pectin and mixtures thereof.

Non-limiting examples of fibers as contemplated by the present teachings include cellulose, viscose, rayon, cellulose acetate, polyamides (i.e. Nylon™), polyalkylenes, polyethylene, polypropylene, bi-component fibers, polyesters, polylactides, polypropanediols, Lyocell™, sphagnum and mixtures thereof.

Non-limiting examples of starch-based absorbents as contemplated by the present teachings include glass-like starches such as disclosed by Huppé et al. (CA 2,308,537); amylopectin networks such as disclosed by Thibodeau et al. (CA 2,462,053); starch agglomerates, hydroxyethyl starch, hydroxypropyl starch, carboxymethyl starch, starch nanocomposites such as disclosed by Berrada et al. (CA 2,483,049); and mixtures thereof.

The synthetic absorbent polymers to be used as co-absorbent materials in the absorbent compositions of the present teachings, are generally obtained from the polymerization, typically by radical or radical graft polymerization, of monomers, non-limiting examples of which include acrylic acid, acrylate salts, acrylic ester, acrylic anhydride, methacrylic acid, methacrylate salts, methacrylic esters, methacrylic anhydride, maleic anhydride, maleic salts, maleate esters, acrylamide, acrylonitrile, vinyl alcohol, vinyl pyrrolidone, vinyl acetate, vinyl guanidine, aspartic acid, aspartic salts and mixtures thereof.

The boronate galactomannan complexes of the present teachings, or absorbent compositions comprising such complexes, are used in methods for absorbing liquids. In an embodiment of the present teachings, one or more of the boronate galactomannan complexes are contacted with a liquid to be absorbed. Non-limiting examples liquids as contemplated by the present teachings include water, aqueous solutions, physiological fluids and saline solutions. The boronate galactomannan complexes, or absorbent compositions comprising such complexes, upon contacting with the liquid(s) to be absorbed, will form a gel trapping the liquid(s) within.

EXPERIMENTAL

Materials

Guar gum (Procol®) was obtained from Polypro (Minneapolis, USA). Phenethyl boronic acid, phenyl boronic acid, trans-1-octen-1-yl boronic acid, cyclohexyl boronic acid, research grade methanol and sodium hydroxide were obtained from Sigma-Aldrich (St-Louis, USA). Hydrochloric acid was obtained from Labmat (Quebec city, Canada).
Convection Oven Samples were dried using a Lab tray drier TY 2, National Drying Machinery Company, (Philadelphia, USA).
Grinder A Braun™ model KSM coffee grinder was used to grind the samples.
Test Methods As discussed in Modern Superabsorbent Polymer Technology (Buchholz F. L. and Graham A. T. Eds., Wiley-VCH, New York, 1998, section 4.6.1. Swelling Capacity: Theory and Practice, p. 147), several methods of measurement are used in order to characterize the swelling capacity of a polymer. In the field of superabsorbents, the Gravimetric Swelling Capacity [also called the Free Swell Capacity (FSC)] and the Centrifuge Capacity [also called the Centrifuge Retention Capacity (CRC)] are recommended methods. The FSC and the CRC were used to compare the swelling capacities of the obtained absorbent products.
Tea Bags for FSC and CRC Measurements Tea bags (10×10 cm) were made from heat sealable Ahlstrom™ filter paper (16.5±0.5) g/m².
FSC Measurements The Free Swell Capacity (FSC) in a 0.9% NaCl solution was determined according to the recommended test method 440.2-02 from EDANA.
CRC Measurements The Centrifuge Retention Capacity (CRC) in a 0.9% NaCl solution was determined according to the recommended test method 441.2-02 from EDANA.

Examples

Comparative Example 1

Phenylboronate Guar Complexes

A mixture comprising guar gum (6.00 g) and water (300 ml) was prepared and left to swell for at least 45 minutes. Phenyl boronic acid (1.34 g) was dissolved in water (40 ml) by increasing the pH of the solution to 13.0 by the addition of an aqueous sodium hydroxide solution (15%). The phenylboronate solution was added to the guar suspension and the resulting suspension stirred 30 minutes. Half of the resulting gel was blended with methanol (300 ml), triturated, and transferred into a beaker. The pH of the suspension was adjusted to 7.9 using hydrochloric acid (10%), under vigorous mechanical stirring. The final suspension was filtered, washed with methanol (3×50 ml), dried overnight in a convection oven at 60° C., and crushed with a mortar to provide a white granular material having a FSC of 51.2 g/g and a CRC of 39.5 g/g.

Comparative Example 2

Phenethylboronate Guar Complexes

A mixture comprising guar gum (6.00 g) and water (300 ml) was prepared and left to swell for at least 45 minutes. Phenethyl boronic acid (1.67 g) was dissolved in water (40 ml) by increasing the pH of the solution to 13.0 by the addition of an aqueous sodium hydroxide solution (15%). The phenethylboronate solution was added to the guar suspension and the resulting suspension stirred 30 minutes. Half of the resulting gel was blended with methanol (300 ml), triturated, and transferred into a beaker. The pH of the suspension was adjusted to 7.9 using hydrochloric acid (10%), under vigorous mechanical stirring. The final suspension was filtered, washed with methanol (3×50 ml), dried overnight in a convection oven at 60° C., and crushed with a mortar to provide a white granular material having a FSC of 62.8 g/g and a CRC of 45.4 g/g.

Comparative Example 3

Trans-1-Octen-1-Ylboronate Guar Complexes

A mixture comprising guar gum (6.00 g) and water (300 ml) was prepared and left to swell for at least 45 minutes. Trans-1-octen-1-ylboronic acid (1.73 g) was dissolved in THF (40 ml). The trans-1-octen-1-ylboronic acid solution was added to the guar suspension. The pH of the suspension was increased to 10.0 by the addition of an aqueous sodium hydroxide solution (15%) and the suspension stirred 30 minutes. Half of the resulting gel was blended with methanol (300 ml), triturated, and transferred into a beaker. The pH of the suspension was adjusted to 8.0 using hydrochloric acid (10%), under vigorous mechanical stirring. The final suspension was filtered, washed with methanol (3×50 ml), dried overnight in a convection oven at 60° C., and crushed with a mortar to provide a white granular material having a FSC of 94.8 g/g and a CRC of 68.4 g/g.

Comparative Example 4

Cyclohexylboronate Guar Complexes

A mixture comprising guar gum (6.00 g) and water (300 ml) was prepared and left to swell for at least 45 minutes. Cyclohexyl boronic acid (1.43 g) was dissolved in water (40 ml) by increasing the pH of the solution to 13.0 by the addition of an aqueous sodium hydroxide solution (15%). The cyclohexylboronate solution was added to the guar suspension and the resulting suspension stirred 30 minutes. Half of the resulting gel was blended with methanol (300 ml), triturated, and transferred into a beaker. The pH of the suspension was adjusted to 7.9 using hydrochloric acid (10%), under vigorous mechanical stirring. The final suspension was filtered, washed with methanol (3×50 ml), dried overnight in a convection oven at 60° C., and ground to provide a white granular material having a FSC of 112.0 g/g and a CRC of 91.0 g/g.

Comparative Example 5 pH Effect on the Performances Characteristics of Phenylboronate Complexes

A mixture comprising guar gum (6.00 g) and water (300 ml) was prepared and left to swell for at least 45 minutes.

Phenyl boronic acid (1.35 g) was dissolved in water (40 ml) by increasing the pH of the solution to 10.0 by the addition of an aqueous sodium hydroxide solution (15%). The phenylboronate solution was added to the guar suspension and the resulting suspension stirred 30 minutes. Half of the resulting gel was blended with methanol (300 ml), triturated, and transferred into a beaker. The pH of the suspension was adjusted to 6.0, 7.0, 8.0, 9.0, 10.0 and 12.0 using hydrochloric acid (10%) and/or sodium hydroxide (15%), under vigorous mechanical stirring. The final suspension was filtered, washed with methanol (3×50 ml), dried overnight in a convection oven at 60° C., and crushed with a mortar to provide a white granular material having the FSC and CRC performance characteristics as illustrated in FIG. 1.

It is to be understood that the invention is not limited in its application to the details of construction and parts as described hereinabove. The invention is capable of other embodiments and of being practiced in various ways. It is also understood that the phraseology or terminology used herein is for the purpose of description and not limitation. Hence, although the present teachings have been described hereinabove by way of illustrative embodiments thereof, it can be modified, without departing from the spirit, scope and nature of the subject teachings as defined in the appended claims.

What is claimed is:

1. An absorbent material comprising one or more dried particles consisting of boronate galactomannan complexes that are precipitated from one or more hydrophilic organic solvents, said dried particles having a size ranging from about 80 µm to about 800 µm, wherein said boronate galactomannan complexes comprise a hydrophobic group, and said dried particles have a Free Swell Capacity (FSC) in a range between 45 g/g and 112.0 g/g and a Centrifuge Retention Capacity (CRC) in a range between 39.5 g/g and 91.0 g/g.

2. The absorbent material of claim 1, wherein the hydrophobic group is selected from the group consisting of aromatic groups, aliphatic groups and cyclic aliphatic groups.

3. The absorbent material of claim 1, wherein the galactomannan is selected from the group consisting of guar gum, locust bean gum, fenugreek gum, tara gum, mesquite gum and mixtures thereof.

4. The absorbent material of claim 3, wherein the galactomannan comprises a galactose to mannose ratio ranging from about 1:5 to about 1:1.

5. A product comprising the absorbent material of claim 1, the product being selected from the group consisting of diapers, incontinence articles, feminine hygiene products, airlaids, absorbent dressings, litter products, absorbent paper products, bandages, surgical pads, and food pads.

6. A method for absorbing liquids, comprising the step of contacting the absorbent material of claim 1 with a liquid selected from the group consisting of water, aqueous solutions, physiological solutions and saline solutions.

7. An absorbent composition comprising at least one absorbent material as defined in claim 1, and at least one co-absorbent material.

8. The absorbent composition of claim 7, wherein the co-absorbent material is selected from the group consisting of synthetic superabsorbent polymers, starch-based absorbents, ionic polysaccharides, fibers and mixtures thereof.

9. A product comprising the absorbent composition of claim 7, the product being selected from the group consisting of diapers, incontinence articles, feminine hygiene products, airlaids, absorbent dressings, litter products, absorbent paper products, bandages, surgical pads, and food pads.

10. A method for absorbing liquids, comprising the step of contacting the absorbent composition of claim 7 with a liquid selected from the group consisting of water, aqueous solutions, physiological solutions and saline solutions.

11. A method for absorbing liquids comprising contacting said liquids with the absorbent composition of claim 7.

12. The method of claim 11, wherein the liquids are selected from the group consisting of water, aqueous solutions, physiological solutions and saline solutions.

13. The absorbent composition of claim 7, wherein the boronate galactomannan complexes are capable of forming a gel upon contacting with a liquid.

14. A method for absorbing liquids comprising contacting said liquids with the absorbent material of claim 1.

15. The method of claim 14, wherein the liquids are selected from the group consisting of water, aqueous solutions, physiological solutions and saline solutions.

16. The absorbent material of claim 1, wherein the boronate galactomannan complexes are capable of forming a gel upon contacting with a liquid.

* * * * *